United States Patent [19]

Leger

[11] Patent Number: 4,517,843

[45] Date of Patent: May 21, 1985

[54] MATERIAL AND COMPONENT TESTING MACHINE

[76] Inventor: Joachim Leger, Adolf-Eiermann-Strasse 13, 6930 Eberbach, Fed. Rep. of Germany

[21] Appl. No.: 552,706

[22] Filed: Nov. 17, 1983

[30] Foreign Application Priority Data

Dec. 1, 1982 [DE] Fed. Rep. of Germany ....... 3244464

[51] Int. Cl.³ .......................... G01N 3/22; G01N 3/20
[52] U.S. Cl. ......................................... 73/847; 73/856
[58] Field of Search ................. 73/847, 848, 856, 860, 73/794, 849, 854

[56] References Cited

U.S. PATENT DOCUMENTS

| 2,042,231 | 5/1936 | Lewis | 73/847 |
| 3,005,336 | 10/1961 | Wyman | 73/860 |
| 4,414,854 | 11/1983 | Haeg | 73/847 |

FOREIGN PATENT DOCUMENTS

| 3204472 | 8/1983 | Fed. Rep. of Germany | 73/854 |
| 1157064 | 5/1958 | France | 73/847 |

Primary Examiner—Anthony V. Ciarlante

Attorney, Agent, or Firm—McCormick, Paulding & Huber

[57] ABSTRACT

Material and component testing machine for providing random length bending and/or torsion loads in preferably bar-shaped test samples, where (a) the test sample 11 is fixed at both ends 12,13 in respective clamping means 14,15;
(b) the one clamping means 14 is situated at the front end 16 of a shaft 17 which is resistant to bending and torsion and rotatable about its longitudinal axis, said shaft being mounted in two preferably hydrostatic bearings attached to the machine frame 19;
(c) a radially projecting lever arm 21 is connected to the rear end 20 of the shaft 17, to which a force Z is applied;
(d) the other clamping means 15 is situated in the center of a yoke 23 which is resistant to bending and torsion, at the back end of which forces X,Y, are applied respectively, each force being at right angles to the other;
(e) the yoke 23 is supported on the machine frame through its two arms 24 via a cardan joint 24-28.

11 Claims, 2 Drawing Figures

MATERIAL AND COMPONENT TESTING MACHINE

BACKGROUND OF THE INVENTION

The invention refers to a material and component testing machine for producing random length bending and/or torsion loads in preferably bar-shaped test samples.

Material testing machines of the type in question are already known in various designs. Here the clamped, bar-shaped test sample is caused to rotate by a drive motor, where it is subjected to a bending and/or torsion load. All known testing machines have the following disadvantages:

With most of the machines, a torsion load in connection with a rotating bending load is not possible. Random length bending load runs, that is, load runs which have loads randomly variable in time, cannot be carried out as the load run usually follows a sinusoidal function and the mean stress of the rotating bending has the value zero. As the test sample has to be caused to rotate and for the overlay of a torsional load, a relatively large apparatus expenditure has to be provided, bearing friction and balance errors coming from production inaccuracies give cause to incorrect test results. The bending moment acting on the test sample is not measured in the direct vicinity thereof, rather from lever arms and a remote applied force. Deviations in the lever geometry and last moments in the force transmission lead to incorrect test results. Tests with already cracked test samples cannot usually be carried out, rather they lead to vibrations in the machine and to useless results due to the asymmetry of the crack.

Furthermore the constructive design of many test machines results in awkward and time consuming change-over of the test sample. Also the measurement value transmission from the rotating shaft to the control and inspection devices is erroneous and subject to defects.

SUMMARY OF THE INVENTION

The invention is based on the task of providing a testing machine of the type in question for materials and components, eliminating the aforementioned disadvantages and which can realize random length bending and/or torsion loads in a more versatile manner with the greatest of accuracy, and which further enables simple inspection of a test sample with internal pressure and/or subjected to certain temperature and corrosion influences. In particular, all types of loads in question have to have an independent effect on the test sample without influencing each other. Furthermore, tests can be carried out where the test sample can be subjected to random length mean stress. Also the measurement value transmission is to take place in a simple manner so as to avoid interference caused by the transmission itself, and other detrimental influences particularly caused by untrue parts and/or balance errors are to be eliminated. Finally it should also be possible to carry out tests with defined loads also in the crack propagation phase.

For solving this task the invention suggests forming the testing machine in the following described manner. The test sample is attached at both ends in a clamping means, one of which is seated on the end of a shaft which is resistant to bending and torsion and rotatable about its longitudinal axis and mounted in two, preferably hydrostatic bearings which are attached to the machine frame. At the end of this shaft a radially projecting lever arm is seated, to which a force is applied in order to subject the test sample to a torsional stress. The other, second clamping means in which the other end of the test sample is held is in the center of a yoke which is resistant to bending and torsion, at the back end of which forces are applied respectively, each force being at right angles to the other.

The outer ends of the yoke are supported by an annular cardan joint, preferably formed as a spring element, surrounding the test sample in a radial plane, at two points lying in an axial plane. The cardan joint or spring element is itself attached to the machine frame at two points which lie in a plane turned through 90°.

Such a testing machine makes it possible to fulfil all aforementioned tasks. It has in particular the advantage that the test sample no longer has to be rotated, meaning considerable simplification in the structure of the machine. This can be seen in particular from the following description and the drawings of a preferred embodiment.

BRIEF DESCRIPTION OF THE DRAWINGS

Further features are shown in the patent claims and from the following description of a testing machine formed according to the invention in a preferred embodiment.

DETAILED DESCRIPTION OF THE DRAWINGS

Figure 1:
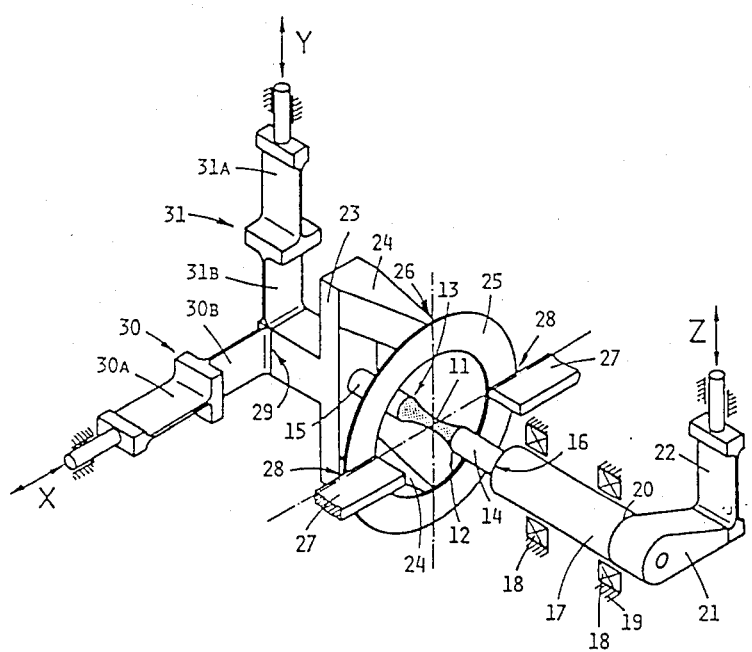
FIG. 1 is a schematic drawing of the principle of the new type of testing machine
Figure 2:
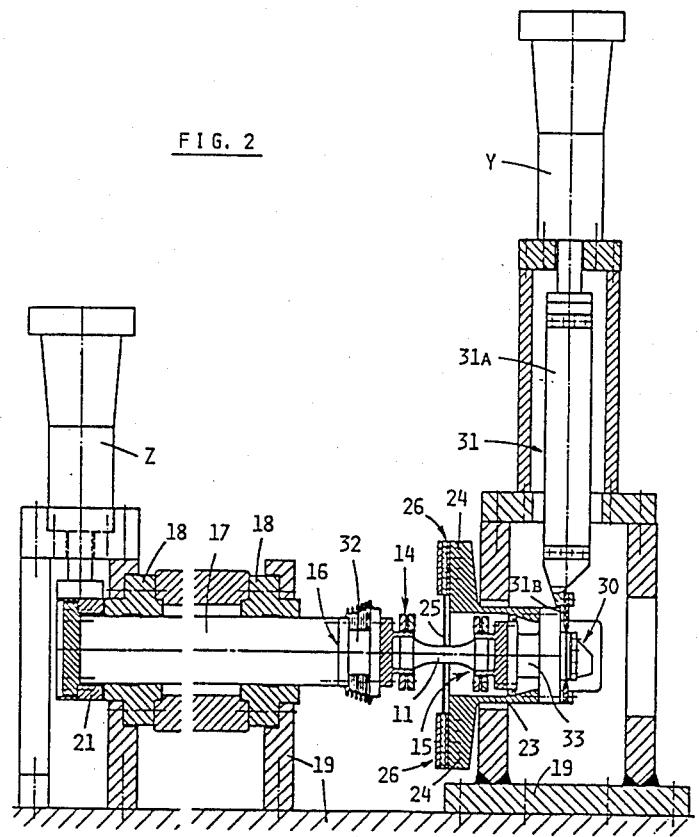
FIG. 2 is a longitudinal section through the testing machine in its general construction.

As FIGS. 1 and 2 show, the test sample 11 is held at both ends 12 and 13 in clamping means 14 and 15 respectively. In the general construction (FIG. 2) the clamping means 14 is connected via a force measuring device 32 for bending about two orthogonal axes and torsion, with the front end 16 of the bending and torsion-resistant shaft 17 which is rotatably mounted about its longitudinal axis in two preferably hydrostatic bearings 18. The bearings 18 are attached to the machine frame.

At the rear end 20 of the shaft 17 there is a radially projecting lever arm 21 on the outer end of which acts a force marked with the arrow Z, which is connected to the arm via a spring band 22.

The second clamping means 15 is connected to the center of the yoke 23 via the second force measuring device 33 for bending (FIG. 2) about two orthogonal axes and torsion.

The yoke 23 is supported on the elastic spring element 25 via its two ends 24, wherein the supporting points 26 lie in a vertical plane. The spring element 25 lies in a plane perpendicular to the test sample longitudinal axis and is connected to the machine frame 19 by the support arms 27, wherein the position of the spring element can be changed in axial direction. The support arms 27 and thus the supporting points 28 for the spring element 25 lie in a horizontal plane.

The yoke 23 is connected to two power sources at its rear end 29, which are marked with the arrows X and Y. The power transmission from the forces X and Y to the cross yoke takes place via the spring bands 30 and 31 respectively which are made up of the two parts 30A and 30B and 31A and 31B respectively, the planes of which are staggered relative to each other through 90° respectively.

The power sources are preferably hydraulic cylinders which make it possible to subject the test sample to a dead weight or pulsating forces. The vibration characteristic properties are such that they can be altered and predetermined in a certain manner.

If the test sample is to be subjected to an internal pressure load, the shaft 17 and the clamping means 14 are provided with appropriate cavities in order to apply a pressurized fluid to the inside of the hollow test sample 11. The constructive arrangement of the testing machine formed according to the invention makes this possible in a simple manner. It is also easy with this design to provide the parts of the machine in the area of the test sample, with a casing so as to provide certain environment conditions to which the test sample will later be exposed.

I claim:

1. A material and component testing machine for providing random length bending and/or torsion loads in preferably bar-shaped testing samples, characterized by the following features:
    (a) clamping means 14, 15 are provided for engaging a test sample at its opposite ends 12, 13 respectively;
    (b) the one clamping means 14 is situated at the front end 16 of a shaft 17 which is resistant to bending and torsion and rotatable about its longitudinal axis and mounted in two bearings 18 attached to the machine frame 19;
    (c) a radially projecting lever arm 21 is connected to the rear end 20 of the shaft 17, to which a power source creating a force Z is connected;
    (d) the other clamping means 15 is situated in the center of a yoke 23 which is resistant to bending and torsion at a back end 29 to which power sources creating forces X,Y are connected respectively, said forces being applied at right angles to each other; and
    (e) the yoke 23 is supported on the machine frame through its two arms 24 via a cardan joint 24-28.

2. A testing machine according to claim 1, wherein the yoke 23 is connected to the machine frame 19 through its two arms 24 via a spring element 25, preferably formed as an annular flat shell, supported on the machine frame 19 via two support arms 27, in a pivotable manner about the connection lines of the support points 26—26, 28—28 lying at right angles to each other and at right angles to the test sample longitudinal axis, however rigid with respect to displacements along these lines as well as rotation about the test samples longitudinal axis.

3. A testing machine according to claim 1, wherein the power sources XYZ are hydraulic cylinders.

4. A testing machine according to claim 1, wherein the power sources XYZ have a random length, predeterminable characteristic.

5. A testing machine according to claim 1, wherein the power sources XYZ are connected to the force introduction points via spring bands 22, 30, 31 which comprise two band parts 30A 30B, 31A 31B staggered through 90°.

6. A testing machine according to claim 1, wherein the shaft 17 is connected to the machine frame 19 via plain bearings, roller bearings or elastic joints.

7. A testing machine according to claim 1, wherein at the rear end 20 of the shaft a torsion power source is applied with a random length, predeterminable characteristic.

8. A testing machine according to claim 1, wherein the clamping means 14 is directly attached to a torsional force source with a random length, predeterminable characteristic.

9. A testing machine according to claim 1, wherein the cardan joint 25,26,28 can be axially displaced along the test sample lonitudinal axis.

10. A testing machine according to claim 1, wherein the cardan joint 25, 26, 28 is located at a selected axial position such that no transverse loads can occur in the test sample and a constant bending load occurs over the test sample longitudinal axis.

11. A testing machine according to claim 1, wherein force measuring means permitting bending about two orthogonal axes and torsion are respectively arranged between the clamping means 14 and the front end 16 of the shaft 17 and between the clamping means 14 and the center of the yoke 23.

* * * * *